United States Patent [19]

Derouane et al.

[11] Patent Number: 5,245,096
[45] Date of Patent: Sep. 14, 1993

[54] PROCESS AND CATALYST FOR PREPARING AROMATIC COMPOUNDS

[75] Inventors: Eric G. Derouane, Namur, Belgium; Robert J. Davis, Melbourne, Fla.; Niels J. Blom, Hillerod, Denmark

[73] Assignee: Haldor Topsoe A/S, Denmark

[21] Appl. No.: 754,532

[22] Filed: Sep. 4, 1991

[30] Foreign Application Priority Data

Sep. 11, 1990 [DK] Denmark ............................. 2175/90

[51] Int. Cl.$^5$ ......................... C07C 5/393; C07C 5/41
[52] U.S. Cl. .................................. 585/419; 585/417; 585/418; 502/84
[58] Field of Search ............... 585/407, 411, 417, 418, 585/419; 502/84

[56] References Cited

U.S. PATENT DOCUMENTS

| | | | |
|---|---|---|---|
| 3,821,105 | 6/1974 | Mitsche et al. | 585/419 |
| 4,774,212 | 9/1988 | Drezdon | 502/84 |
| 4,843,168 | 6/1989 | Drezdzon et al. | 585/444 |
| 4,866,019 | 9/1989 | van Broekhoven | 502/84 |
| 4,923,837 | 5/1990 | Fukuhara | 502/84 |
| 5,026,921 | 6/1991 | Degnan, Jr. et al. | 585/418 |
| 5,079,203 | 1/1992 | Pinnavaia | 502/80 |

FOREIGN PATENT DOCUMENTS 0330224 8/1989 European Pat. Off. .

OTHER PUBLICATIONS

Reichle, "Catalytic Reactions by Thermally Actuated Synthetic Anionic Clay", J. of Catalysis, 94, 547–557 (1985).

Primary Examiner—Anthony McFarlane
Attorney, Agent, or Firm—Ostrolenk, Faber, Gerb & Soffen

[57] ABSTRACT

A process for preparing aromatic compounds, wherein a gaseous feed containing $C_6$ to $C_{20}$ hydrocarbons is reacted in the presence of a catalyst, which catalyst comprises a metal from Group VIII of the Periodic Table loaded on a hydrotalcite-type support material having in its uncalcined state the general formula

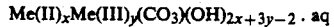

$$Me(II)_xMe(III)_y(CO_3)(OH)_{2x+3y-2} \cdot aq$$

with an x-ray diffraction (d003) greater than about 7.4 Angstroms, and wherein
Me(II) is at least one divalent metal selected from the group comprising copper, magnesium, manganese, zinc and a metal from Group VIII of the Periodic Table;
Me(III) is at least one trivalent metal selected from the group comprising aluminum, chromium and iron; and
x and y are positive numbers satisfying the following relationship $x/y \geq 0.5$.

8 Claims, No Drawings

PROCESS AND CATALYST FOR PREPARING AROMATIC COMPOUNDS

BACKGROUND OF THE INVENTION

1. Field of the Invention

The present invention relates to the preparation of aromatic compounds by reacting gaseous feed containing $C_6$ to $C_{20}$ hydrocarbons in the presence of a catalyst.

In particular the present invention involves a novel catalyst comprising a metal from Group VIII of the Periodic Table loaded on hydrotalcite-type derived material.

2. Description of the Related Art

Presently, most used aromatization catalysts are metal oxides, usually chromia, deposited on alumina and reduced metals of Group VIII in the Periodic Table supported on alumina, silica or activated carbon.

Other catalysts have been suggested in the art. Zeolitic aromatization catalysts loaded with a Group VIII metal are mentioned in U.S. Pat. No. 4,104,320; U.S. Pat. No. 4,448,891 and U.S. Pat. No. 4,822,762.

Danish Patent Application No. 89/6666 discloses a metal sulphide modified zeolite of ZSM-5 type useful as catalyst in the conversion of aliphatic hydrocarbons to aromatic compounds.

So far known, aromatization processes employing catalysts based on hydrotalcite-type derived materials comprising a Group VIII metal for use in the preparation of aromatic compounds, have not been recognized in the art.

SUMMARY OF THE INVENTION

Thus, an object of the present invention is to provide a process for preparing aromatic compounds, wherein a gaseous feed containing $C_6$ to $C_{20}$ hydrocarbons is reacted in the presence of a catalyst, which catalyst comprises as catalytically active material a metal from Group VIII of the Periodic Table loaded on a hydrotalcite-type derived support material having in its uncalcined state the general formula $$Me(II)_x Me(III)_y (CO_3)(OH)_{2x+3y-2} \cdot aq$$

with an x-ray diffraction (d003) greater than about 7.4 Angstroms, and wherein

Me(II) is at least one divalent metal selected from the Group comprising copper, magnesium, manganese, zinc and a metal from Group VIII of the Periodic Table;

Me(III) is at least one trivalent metal selected from the Group comprising aluminum, chromium and iron;

x and y are positive numbers satisfying the following relationship $x/y \geq 0.5$.

A further object of the present invention is to provide a new catalyst for use in the above process, which catalyst having as its active ingredient a metal from Group VIII of the Periodic Table supported on a hydrotalcite-type material with the above definitions.

DETAILED DESCRIPTION OF THE PREFERRED EMBODIMENTS

Hydrotalcite-type materials belong to the Group of anionic clay minerals having the general formula as briefly stated herein before.

The structure of these minerals is composed of infinite layers with positively charged metal oxide-hydroxide layers with alternating interlayers of water and carbonate ions. In the metal oxide-hydroxide layers a part of the divalent metal ions is replaced by trivalent metal ions gaining positive charge, which is compensated for by the interstitially carbonate and hydroxide ions.

The hydrotalcite-type materials of this invention may be prepared by a coprecipitation procedure, in which an aqueous solution containing divalent and trivalent metals is precipitated with an aqueous solution of alkali metal hydroxide and an alkali metal carbonate and/or alkali metal hydrogen carbonate at a pH value of between about 7.0 and about 10.0 and a temperature from about 20° to 80° C.

Salts of the divalent metal Me(II) including magnesium, copper, maganese, zinc and Group VIII metal salts and salts of the trivalent metal Me(III), including aluminum, chromium and iron salts are combined in an aqueous solution, either alone or in combinations thereof and coprecipitated as described above. The molar ratio of Me(II)/Me(III) is, thereby, $\geq 0.5$, preferably between about 0.5 and 20.

Preferred salts are the nitrates of the above metals.

The resulting precipitated material is recovered by filtration after precipitation when using an aqueous solution of alkali metal hydroxide and alkali metal carbonate.

When using precipitation only with an alkali metal hydroxide solution, the precipitated material is further dispersed in a stirred aqueous alkali metal carbonate solution, and/or alkali metal hydrogen carbonate solution for about 10-70 hours before filtration.

The amount and concentration of the alkali metal carbonate solution should at least contain an amount of carbonate ion, which meets the stoichiometry of the structure of the desired hydrotalcite-type material.

Following the precipitation, the obtained product is washed with water to remove excess of ions derived from the starting materials.

The X-ray diagrams of the dried and uncalcined hydrotalcite-type products, in which the products have by way of example the composition $$Zn_3CuAl_2(OH)_{12}CO_3 \cdot aq; \text{ and}$$

$$Mg_{10}Al_2(OH)_{24}CO_3 \cdot aq;$$

are summarized in Table 5 below and indicate a layered structure similar to that of hydrotalcite clay

TABLE 1

| $Zn_3CuAl_2(OH)_{12}CO_3.aq$ | | $Mg_{10}Al_2(OH)_{24}CO_3.aq$ | | $Mg_6Al_2(OH)_{16}CO_3.4H_2O$ | |
|---|---|---|---|---|---|
| d/Å | I/Io | d/Å | I/Io | d/Å | I/I |
| 7.54 | 100 | 7.66 | 100 | 7.84 | 100 |
| 3.77 | 54 | 3.83 | 67 | 3.90 | 60 |
| 2.59 | 53 | 2.58 | 73 | 2.60 | 40 |
| 2.29 | 34 | 2.31 | 27 | 2.33 | 25 |
| 1.94 | 24 | 1.95 | 15 | 1.99 | 30 |
| 1.54 | 11 | 1.52 | 49 | 1.54 | 35 |
| 1.50 | 14 | 1.49 | 38 | 1.50 | 25 |

TABLE 1-continued

| $Zn_3CuAl_2(OH)_{12}CO_3.aq$ | | $Mg_{10}Al_2(OH)_{24}CO_3.aq$ | | $Mg_6Al_2(OH)_{16}CO_3.4H_2O$ | |
|---|---|---|---|---|---|
| d/Å | I/Io | d/Å | I/Io | d/Å | I/I |
| 1.42 | 5 | 1.42 | 6 | 1.42 | 8 |

Even though there are some variations in the X-ray powder diffraction patterns of the hydrocalcite-type materials, certain lines in the diffraction patterns are characteristic for these materials.

The characteristic lines are shown in Table 2:

TABLE 2

| d/Å | I/Io |
|---|---|
| >7.4 | vs |
| >3.7 | s |
| 2.59 ± 0.1 | s |
| 2.30 ± 0.05 | M |
| 1.96 ± 0.05 | mW |

Calcination of the obtained hydrotalcite-type materials leads to substantially homogeneous metal oxide-hydroxide mixtures with a higher surface area than the uncalcined hydrotalcite-type materials.

During the calcination step the temperature has to be chosen carefully. High temperatures leading to separate phases of metal oxides and spinels have to be avoided. The X-ray diagrams of the materials calcined at the appropriate temperature do not contain any lines for formed spinels.

A Group VIII metal is loaded on the calcined material by preferably aqueous impregnation with a soluble Group VIII metal salt, including salts of platinum and palladium.

Suitable salts of Group VIII metals are those, which upon heating to about 400° C. give the oxides of the metals, such as chlorides, nitrates and other simple salts.

Preferred salts of platinum and palladium, are the coordinated salts, such as the aminoacetates, tetrammine chlorides or tetrammine nitrates.

The Group VIII metal is loaded on the support material in any catalytically active amount. Convenient amounts of Group VIII metal in the catalyst will range between about 0.01 to about 10 percent by weight (wt %) of the weight of the material, preferably between about 0.1 to about 5 wt %, and most preferred between about 0.1 to about 2 wt %.

When used as catalyst in the inventive process the above obtained materials are activated in a hydrogen containing atmosphere at a temperature of between about 100° C. and 450° C.

The process of the present invention is accomplished by contacting a hydrocarbon feedstream, comprising $C_6$-$C_{20}$ paraffinic hydrocarbons, with the catalyst as defined above. The catalyst is, thereby, arranged in a reaction zone, such as a fixed bed reactor or a fluidized bed reactor.

The process may be carried out at a temperature of between 100°-600° C., preferably of about 350°-500° C. The reaction can take place at a pressure of 0-100 bar, preferably, about 0-10 bar and a weight space velocity (WSHV) of about 0.01 to 200, preferably, 0.01 to 10 depending on the amount and shape of the catalyst. The catalyst may, thereby, be composed with a matrix binder, such as clays, alumina, silica, titania, magnesia or compositions thereof and can be employed in any shape, such as particles, pellets or pressed tablets. In large reactor units, it might be preferred to use the catalyst loaded on monolithic structures, known in the art.

In the reaction zone the feedstream is converted to aromatic compounds at a conversion level of about 10 to about 100% per pass depending on the weight space velocity of the feedstream.

Produced aromatic compounds are recovered from the effluent of the reaction zone and unconverted hydrocarbon feed together with paraffinic, olefinic and napthenic hydrocarbons (PON) by-products are recycled back to the reaction zone.

The above objects and features of the present invention are further illustrated by the following Examples.

In Examples 1-22 are prepared platinum and palladium loaded hydrotalcite-type aromatization catalysts according to an embodiment of the invention and in Examples 23a and 23b comparison catalysts having platinum loaded on metal oxide—metal spinel support.

The catalysts are characterized by their chemical composition and by their X-ray powder diffraction in their uncalcined and calcined state.

The X-ray powder diffraction pattern was determined by standard techniques using the radiation of the K-alpha doublet of copper.

Examples 24-36 are carried out by a process for preparation of aromatic compounds according to an embodiment of the invention employing the catalysts prepared in Examples 1-23b.

In the Process Examples feed gas consisting of n-hexane and hydrogen in a molar ratio $H_2/C_6$ of 6, n-heptane and hydrogen in a molar ratio $H_2/C_7$ of 3, or pure n-heptane, is passed through a reaction zone containing 1.0 g samples of the above catalysts crushed to particles of 0.15-0.71 mm diameter (Mesh 25-100) and loaded in a quartz tube reactor with an inner diameter of 6 mm. Aromatic compounds together with non-aromatizable $C_1$-$C_5$ hydrocarbons are recovered from the reactor effluent. Unconverted feed and converted hydrocarbons comprising paraffins, olefins and napthenes (PON), are recycled to the reactor inlet.

The product selectivity for aromatic compounds was calculated on the amount of hydrocarbons in the not recycled reactor effluent, by dividing the fractional conversion of the feed to aromatics with the total amount of not recycled hydrocarbons in the effluent.

EXAMPLE 1

Preparation of $Mg_4Al_2(OH)_{12}CO_3$ . aq hydrocalcite-type material.

A solution of 200 g KOH in 600 ml water was added at ambient temperature to a stirred solution of 256.4 g $Mg(NO_3)_2$ . $6H_2O$ and 187.5 g $Al(NO_3)_3$ . $9H_2O$ in 500 ml water. The resulting slurry was kept at 40° C. for 1 hour with stirring.

75 g $KHCO_3$ in 500 ml water were then added to the slurry, which was heated to 80° C. with stirring, giving a final pH of 8.0. After about 3 hours the slurry was filtered and the precipitate added to 2000 ml water at 80° C. After about 18 hours, a solid crystalline product, having an X-ray powder diffraction pattern as shown hereinbefore in Table 2 and chemical analysis values as summarized below, was separated by filtration, washed with water and dried at 100° C. for 24 hours.

Chemical analysis: 19.0 wt % Mg, 10.5 wt % Al and 1.88 wt % K, giving the above composition formula.

EXAMPLES 2-3

Preparation of $Mg_{10}Al_2(OH)_{24}CO_3$ . aq hydrocalcite-type material.

A solution of 112 g KOH and 10.35 g $K_2CO_3$ in 1000 ml water was added at ambient temperature to a stirred solution of 217.6 g $Mg(NO_3)_2$ . $6H_2O$ and 56.25 g $Al(NO_3)_3$ . $9H_2O$ in 1000 ml water. A part of the resulting slurry was kept at ambient temperature for 18 hours giving a final pH of 8.8 (Example 2) or the residue was heated to 65° C. under stirring for 18 hours giving a final pH of 9.3 (Example 3). Thereafter, each of the slurries was filtered, washed with water and dried at 120° C. for 18 hours.

X-ray of the obtained crystalline products show the lines of Table 2.

Chemical analysis of the product showed the following results: 28.9 wt % Mg, 6.5 wt % Al and 0.81 wt % K, giving the above composition formula.

EXAMPLE 4

Preparation of $Mg_{10}Al_2(OH)_{24}CO_3$ . aq hydrocalcite-type material.

A reaction mixture was prepared by adding simultaneously a solution prepared by dissolving 217.6 g $Mg(NO_3)_2$ . $6H_2O$ and 56.25 g $Al(NO_3)_3$ . $9H_2O$ in 1000 ml water, and a solution prepared by dissolving 112 g KOH and 10.35 g $K_2CO_3$ in 1000 ml water to a stirred beaker, kept at 65° C. for 15 min.

The resulting crystalline precipitate, having the X-ray powder diffraction pattern as shown in Table 2, was separated by filtration, washed with water and dried at 80° C. for 4 hours.

Chemical analysis of the product showed the following results: 18.6 wt % Mg, 3.65 wt % Al and 1.2 wt % K giving the above composition formula.

EXAMPLE 5

Preparation of $Mg_6Fe_2(OH)_{16}CO_3$ . aq hydrocalcite-type material.

A solution of 180 g KOH in 1000 ml water was added at ambient temperature to a stirred solution of 308 g $Mg(NO_3)_2$ . $6H_2O$ and 162 g $Fe(NO_3)_3$ . $9H_2O$ in 1000 ml water. 5 min. with stirring. 40 g $KHCO_3$ in 300 ml water were then added to the slurry, which thereafter was heated to 55° C. under stirring, giving a final pH of 8.29. After about 2 hours the slurry was filtered and the precipitate added to a solution of 20 g $KHCO_3$ in 2000 ml water and the mixture heated for 24 hours at 55° C. A solid crystalline product having an X-ray powder diffraction pattern as summarized in Table 2, was separated by filtration, washed with water and dried at 80° C. for 16 hours.

EXAMPLE 6

Preparation of $Zn_2Al_3(OH)_{12}CO_3$ . aq hydrocalcite-type material.

A solution of 5.9 kg KOH in 3.6 l water was added within 2-5 min. at ambient temperature to a stirred solution containing 1.3 kg ZnO, 3.4 kg $HNO_3$ (62%) and 9.0 kg $Al(NO_3)$ . $9H_2O$ in 36 l water. The pH value of the resulting slurry was adjusted to 7.0 by addition of $KOH/HNO_3$.

To the slurry was added a solution of 1.6 kg $KHCO_3$ in 12 l water, and the mixture heated at 55° C. After about 2 hours the mixture was filtered and the resulting precipitate added to a solution 0.8 kg KOH in 10 l water. This mixture was then heated to 55° C. for 16 hours with stirring.

A solid crystalline product having an X-ray powder diffraction pattern shown in Table 2 and chemical analysis values as summarized below, was separated by filtration, washed with water and dried at 80° C. for 66 hours.

Chemical analysis: 29.6 wt % Zn, 18.6 wt % Al, 6.7 wt % $CO_3$ and 85 ppm K.

EXAMPLE 7

Preparation of $Zn_6Al_2(OH)_{16}CO_3$ . aq hydrocalcite-type material.

A solution of 41.5 g KOH in 500 ml water was added at ambient temperature to a stirred solution of 70 g $Zn(NO_3)_2$ . $6H_2O$ and 30 g $Al(NO_3)_3$ . $9H_2O$ in 500 ml water. The resulting slurry was kept at ambient temperature with stirring. After about 10 min. the slurry was filtered. The resulting precipitate was added to a solution of 10 g $KHCO_3$ in 1000 ml water at 65° C., giving a final pH of 9.0.

After about 16 hours a solid crystalline product having an X-ray powder diffraction pattern as shown in Table 2 and chemical analysis values as summarized below, was separated by filtration, washed with water and dried at 80° C. for 24 hours.

Chemical analysis: 45.6 wt % Zn, 6.4 wt % Al and 9.7 wt % $CO_3$, giving the above composition formula.

EXAMPLE 8

Preparation of $CuZn_3Al_2(OH)_{12}CO_3$ . aq hydrotalcite-type material.

A solution of 395 g KOH in 3000 ml water was added at ambient temperature to a stirred solution of 120.5 g $Cu(NO_3)_2$ . $3H_2O$, 446.2 g $Zn(NO_3)_2$ . $6H_2O$ and 375 g $Al(NO_3)_3$ . $9H_2O$ in 3000 ml water. The resulting slurry was kept at ambient temperature for 5 min. with stirring.

100 g $KHCO_3$ in 1000 ml water were then added to the slurry, and the mixture then heated to 55° C. with stirring, giving a final pH of 7.47. After about 2 hours the mixture was filtered and the precipitate added to a solution of 50 g $KHCO_3$ in 6000 ml water. This mixture was heated for 72 hours at 55° C. A solid crystalline product having an X-ray powder diffraction pattern as shown in Table 2 and chemical analysis values as summarized below, was separated by filtration, washed with water and dried at 120° C. for 18 hours.

Chemical analysis: 10.0 wt % Cu, 29.4 wt % Zn, 9.0 wt % Al and 9.3 wt % $CO_3$, giving the above composition formula.

EXAMPLE 9

Preparation of $Zr_4Cr_2(OH)_{12}(CO_3)$ . aq hydrocalcite-type material.

A solution of 395 g KOH in 2500 ml water was added at ambient temperature to a stirred solution of 595 g $Zn(NC_3)_2$ . $6H_2O$ and 400 g $Cr(NO_3)_3$ . $9H_2O$ in 2500 ml water. The resulting slurry was kept at ambient temperature for 15 min. with stirring. 100 g $KHCO_3$ in 1000 ml distilled water were then added to the slurry. The mixture was then heated to 55° C. under stirring, giving a final pH of 7.34. After about 2 hours the mixture was filtered and the precipitate added to a solution of 50 g $KHCO_3$ in 5000 ml water. This mixture was then heated at 55° C. for 24 hours. A solid crystalline product having an X-ray powder diffraction pattern as shown in Table 2 and chemical analysis values as summarized below, was separated by filtration, washed with water and dried at 120° C. for 18 hours.

Chemical analysis: 37.1 wt % Zn, 15.2 wt % Cr and 8.3 wt % $CO_3$ 75 ppm K; giving the above composition formula.

EXAMPLE 10

Preparation of $Mg_{20}Al_2(OH)_{44}CO_3$. aq hydrocalcite-type material.

A reaction mixture was prepared by adding simultaneously a solution prepared by dissolving 217.6 g $Mg(NO_3)_2 \cdot 6H_2O$ and 3.19 g $Al(NO_3)_3 \cdot 9H_2O$ in 1000 ml water, and a solution prepared by dissolving 112 g KOH and 10.4 g $K_2CO_3$ in 1000 ml water to a stirred beaker, and kept at 65° C. for 15 min.

The resulting precipitate was separated by filtration, washed with water and dried at 120° C. for 18 hours, leaving the above crystalline product with an X-ray powder diffraction pattern as shown in Table 2. Chemical analysis of the product showed the following results: 34.3 wt % Mg, 3.8 wt % Al and 1.2 wt % K, giving the above composition formula.

EXAMPLES 11-22

Preparation of Group VIII aromatization catalysts loaded on hydrotalcite-type derived material according to the invention.

The catalysts of these Examples were prepared by calcination of the hydrotalcite-type materials obtained in Examples 1-10 and impregnation with a Group VIII metal solution.

The materials were calcined in air at 450°-600° C. for 4-12 hours, as further specified in Table 3, which follows.

In the X-ray powder diffraction patterns of the calcined materials, no lines for formed spinels were found.

The calcined products were crushed to particles with a particle size of about 0.15-0.71 mm (25-100 Mesh), and impregnated with a platinum (Examples 11-19 and 22), or a palladium (Examples 20-21) solution.

A platinum solution and palladium solution for impregnating the particulate materials were prepared by dissolving 2 g Pt $(NH_3)_4(NO_3)_2$ and 32 g Pd $(NH_3)_4(NO_3)_2$, respectively, in 500 ml water.

2 g samples of the calcined particulate material were immersed in the above solutions for about 18 hours, then filtered, dried and calcined at 450° C. for 4 hours in air.

The amounts of Pt or Pd impregnated on the materials are further specified in Table 3.

The Pt and Pd-aromatization catalysts, thus obtained, were activated in hydrogen atmosphere at 120° C. for about 30 min., followed by calcination in a hydrogen atmosphere at 425° for about 2 hours.

TABLE 3

| Catalyst Example No. | Hydrotalcite-type material Example No. | Temp/ °C. | Calcination Time/h | wt % (§) of % Pt or Pd in catalyst |
|---|---|---|---|---|
| 11 | 1 | 600 | 12 | 0,75 (Pt) |
| 12 | 2 | 600 | 12 | 0,69 (Pt) |
| 13 | 3 | 600 | 12 | 0,82 (Pt) |
| 14 | 4 | 600 | 12 | 0,74 (Pt) |
| 15 | 5 | 450 | 6 | 0,92 (Pt) |
| 16 | 6 | — | — | 0,41 (Pt) |
| 17 | 7 | 450 | 4 | 0,62 (Pt) |
| 18 | 8 | 450 | 4 | 0,75 (Pt) |
| 19 | 9 | 500 | 6 | 0,81 (Pt) |
| 20 | 10 | 500 | 8 | 0,79 (Pd) |
| 21 | 10 | 500 | 4 | 0,81 (Pd) |
| 22 | 1 | 450 | 6 | 0,67 (Pt) |

(§) calculated on the total amount of loaded catalyst

EXAMPLE 23a

Preparation of a comparison magnesium oxide-magnesium aluminum-spinel catalyst.

The hydrotalcite-type material obtained in Example 1 was calcined at 900° C. for 6 hours in air. X-ray powder diffraction pattern (Table 4) of the calcined material shows distinctive lines of magnesium aluminum-spinel and magnesium oxide(*).

TABLE 4

| d/Å | I/Io |
|---|---|
| 4.69 | 15 |
| 2.85 | 22 |
| 2.44 | 66 |
| 2.11* | 100 |
| 2.03 | 47 |
| 1.64 | 4 |
| 1.56 | 22 |
| 1.49* | 45 |
| 1.43 | 37 |

The magnesium oxide-magnesium aluminum-spinel support material, thus obtained, was loaded with platinum by a procedure similar to that of Example 11.

The final platinum loaded magnesium aluminum-spinel comparison catalyst containing 0.76 wt % Pt was activated as described above under Examples 11-22.

EXAMPLE 23b

Preparation of a comparison ZnAl-spinel catalyst.

The hydrotalcite-type material obtained in Example 6 was calcined at 900° C. for 6 hours in air.

X-ray powder diffraction pattern (Table 5) of the calcined material shows distinctive lines of zinc aluminum-spinel and zinc oxide(*).

TABLE 5

| d/Å | I/Io |
|---|---|
| 4.67 | 2 |
| 2.85 | 66 |
| 2.81(*) | 17 |
| 2.47(*) | 24 |
| 2.44 | 100 |
| 1.63 | 8 |
| 1.56 | 33 |
| 1.48* | 5 |
| 1.43 | 34 |

The zinc oxide zinc aluminum-spinel support material was loaded with platinum (0.65 wt %), as described hereinbefore (Example 11) and activated as under Examples 11-22.

EXAMPLES 24-36

The performance of the catalysts prepared in Examples 11-22 and the comparison catalysts of Examples 23a and 23b were tested in the conversion of n-hexane or n-heptane to aromatic compounds. The aromatization process was carried out as described hereinbefore. Further process conditions and the results of the reactions are shown in Table 6 below, where "aromatics" includes benzene, toluene and xylenes.

TABLE 6

|  | Example No. | | | | | | | |
|---|---|---|---|---|---|---|---|---|
|  | 24 | 25 | 26 | 27 | 28 | 29 | 30 | 31 |
| Catalyst, Example No. | 11 | 12 | 14 | 13 | 15 | 16 | 17 | 18 |
| On stream time, hr | 1 | 1 | 1 | 3 | 2 | 1 | 1 | 1 |
| Feed | $H_2/C_6H_{14}$ | $H_2/C_6H_{14}$ | $H_2/C_6H_{14}$ | $H_2/C_6H_{14}$ | $H_2/C_6H_{14}$ | $H_2/C_6H_{14}$ | $H_2/C_6H_{14}$ | $H_2/C_6H_{14}$ |
| $H_2/C_6H_{14}$ mole ratio | 6 | 6 | 6 | 6 | 6 | 6 | 6 | 6 |
| $H_2/C_7H_{16}$ mole ratio | | | | | | | | |
| WHSV $C_6H_{14}$ | 1.32 | 2.11 | 2.11 | 2.11 | 3.3 | 2.11 | 2.11 | 2.11 |
| WHSV $C_7H_{16}$ | | | | | | | | |
| Temp. °C. | 451 | 475 | 475 | 475 | 404 | 475 | 475 | 475 |
| Conversion, % | 40.73 | 48.99 | 54.63 | 53.11 | 10.87 | 22.74 | 23.19 | 13.11 |
| Product Composition/ Feed Free Basis wt % | | | | | | | | |
| $C_1-C_5$ | 12.66 | 9.08 | 10.71 | 8.93 | 9.90 | 4.01 | 2.67 | 3.01 |
| $C_1-C_4$ | 0.58 | 1.61 | 1.88 | 1.43 | 3.42 | 2.86 | 2.55 | 2.61 |
| $C_6$ + PON | 32.46 | 37.14 | 34.37 | 46.25 | 72.29 | 72.34 | 79.98 | 85.89 |
| Aromatics | 54.30 | 52.17 | 53.04 | 43.40 | 14.39 | 20.75 | 14.79 | 8.49 |
| Selectivity, % Aromatics | 80.39 | 82.98 | 80.81 | 80.74 | 51.92 | 75.12 | 73.92 | 60.18 |

|  | Example No. | | | | | |
|---|---|---|---|---|---|---|
|  | 33 | 34 | 35 | 36 | 37 | 38 |
| Catalyst, Example No. | 19 | 20 | 21 | 21 | 22 | 23a | 23b |
| On stream time, hr | 1 | 4 | 1 | 2 | 1 | 2 | 1 |
| Feed | $H_2/C_6H_{14}$ | $H_2/C_6H_{14}$ | $C_7H_{16}$ | $H_2/C_6H_{14}$ | $H_2/C_6H_{14}$ | $H_2/C_6H_{14}$ | $H_2/C_6H_{14}$ |
| $H_2/C_6H_{14}$ mole ratio | 6 | 6 | | | 6 | 6 | 6 |
| $H_2/C_7H_{16}$ mole ratio | | | | 3 | | | |
| WHSV $C_6H_{14}$ | 2.11 | 2.64 | | | 2.11 | 2.11 | 2.11 |
| WHSV $C_7H_{16}$ | | | 0.91 | 0.91 | | | |
| Temp. °C. | 475 | 480 | 450 | 485 | 475 | 475 | 475 |
| Conversion, % | 29.33 | 33.10 | 12.30 | 22.84 | 64.61 | 28.46 | 9.3 |
| Product Composition/ Feed Free Basis wt % | | | | | | | |
| $C_1-C_5$ | 2.08 | 13.24 | 0.78 | 5.33 | 12.57 | 8.49 | 2.96 |
| $C_1-C_4$ | 2.00 | 1.94 | 0.00 | 0.17 | 1.23 | 1.42 | 2.08 |
| $C_6$ + PON | 82.41 | 14.20 | 5.87 | 4.92 | 17.43 | 46.75 | 90.31 |
| Aromatics | 13.51 | 70.62 | 6.04 | 12.77 | 68.77 | 43.33 | 4.65 |
| Selectivity, % Aromatics | 76.83 | 82.31 | 88.55 | 69.88 | 83.29 | 81.38 | 48.0 |

The above data show that higher conversion rates and improved selectivity for formation of aromatic compounds are obtained by use of MgAl hydrotalcite (Examples 24, 25, 33) and ZnAl hydrotalcite (Example 30) supported catalysts according to the invention, when compared with the conversion rates and selectivity obtained by use of the respective magnesium oxide—magnesium aluminum spinel and zinc oxide—zinc aluminum spinel comparison catalysts of Examples 23a, 23b.

We claim:

1. A process for preparing aromatic compounds, wherein a gaseous feed containing $C_6$ to $C_{20}$ hydrocarbons is reacted in the presence of a catalyst, which catalyst comprises a metal from Group VIII of the Periodic Table loaded on a support material made by calcining a compound of the general formula

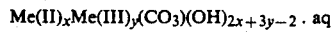

Me(II)$_x$Me(III)$_y$(CO$_3$)(OH)$_{2x+3y-2}$ · aq with an x-ray diffraction (d003) before calcination greater than about 7.4 Angstroms, and wherein
Me(II) is at least one divalent metal selected from the group consisting of copper, magnesium, manganese, zinc and a metal from Group VIII of the Periodic Table;
Me(III) is at least one trivalent metal selected from the group consisting of aluminum, chromium and iron; and
x and y are positive numbers satisfying the following relationship x/y ≧ 0.5.

2. The process of claim 1, wherein x/y is between about 0.5 to 20.

3. The process of claim 1, wherein the divalent metal Me(II) is magnesium or a combination of magnesium with at least one divalent metal selected from the group consisting of copper, manganese and zinc.

4. The process of claim 1, wherein the divalent metal Me(II) is zinc or a combination of zinc with divalent copper.

5. The process of claim 1, wherein the trivalent metal Me(III) is iron or chromium.

6. The process of claim 1, wherein the divalent metal Me(II) is magnesium and the trivalent metal Me(III) is aluminum.

7. The process of claim 1, wherein the Group VIII metal loaded on the support material is selected from the group consisting of platinum, palladium and combinations thereof.

8. The process of claim 1, wherein the compound is calcined at about 400°–600° C.

* * * * *